United States Patent
Nikolaev et al.

(10) Patent No.: US 11,357,825 B2
(45) Date of Patent: Jun. 14, 2022

(54) MEANS FOR TREATING CARDIOVASCULAR DISEASE

(71) Applicant: Universitaetsklinikum Hamburg-Eppendorf, Hamburg (DE)

(72) Inventors: Viacheslav Nikolaev, Hamburg (DE); Alexander Froese, Hannover (DE)

(73) Assignee: Universitaetsklinikum Hamburg-Eppendorf, Hamburg (DE)

( * ) Notice: Subject to any disclaimer, the term of this patent is extended or adjusted under 35 U.S.C. 154(b) by 94 days.

(21) Appl. No.: 16/627,445

(22) PCT Filed: Jul. 9, 2018

(86) PCT No.: PCT/EP2018/068491
§ 371 (c)(1),
(2) Date: Dec. 30, 2019

(87) PCT Pub. No.: WO2019/011833
PCT Pub. Date: Jan. 17, 2019

(65) Prior Publication Data
US 2020/0297814 A1 Sep. 24, 2020

(30) Foreign Application Priority Data
Jul. 9, 2017 (EP) .................................. 17180406

(51) Int. Cl.
*A61K 38/17* (2006.01)
*A61P 9/06* (2006.01)
*A61P 9/10* (2006.01)
*A61K 31/165* (2006.01)
*A61K 31/21* (2006.01)
*A61K 31/138* (2006.01)

(52) U.S. Cl.
CPC ........ *A61K 38/1774* (2013.01); *A61K 31/165* (2013.01); *A61K 31/21* (2013.01); *A61P 9/06* (2018.01); *A61P 9/10* (2018.01); *A61K 31/138* (2013.01)

(58) Field of Classification Search
CPC .. A61K 38/1774; A61K 31/165; A61K 31/21; A61K 31/138; A61P 9/10; A61P 9/06
USPC ........................................................ 514/619
See application file for complete search history.

(56) References Cited

PUBLICATIONS

International Search Report dated Aug. 21, 2018, in International Application No. PCT/EP2018/068491.
Jaekyu Shin et al: "Beta-Blocker pharmacogenetics in heart failure", Heart Failure Reviews, Kluwer Academic Publishers, BO, vol. 15, No. 3, Apr. 24, 2008 (Apr. 24, 2008), pp. 187-196, XP019789609, ISSN: 1573-7322, the whole document, in particular, table 2.
Dinicolantonio James et al: "Meta-Analysis of Carvedilol Versus Beta 1 Selective Beta-Blockers (Atenolol, Bisoprolol, Metoprolol, and Nebivolol)", American Journal of Cardiology, Cahners Publishing Co., Newton, MA, US, vol. 111, No. 5, Jan. 4, 2013 (Jan. 4, 2013), pp. 765-769, XP028978485, ISSN: 0002-9149, DOI: 10.1016/J.AMJCARD.2012.11.031, the whole document, in particular, p. 765.
Jahns R. et al: "Modulation of Beta1-Adrenoceptor Activity by Domain-Specific Antibodies and Heart Failure-Associated Autonatibodies", Journal of the American College of Cardio, Elsevier, New York, NY, US, vol. 36, No. 4, Oct. 1, 2000 (Oct. 1, 2000), pp. 1280-1287, XP009072151, ISSN: 0735-1097, DOI: 10.1016/S0735-1097(00)00881-0, the whole document, in particular, pp. 1284-1285.
Archana Dhyani: "Preparation and Characterization of Atenolol Laden Nanoparticles", Journal of Nanomedicine Research, vol. 4, No. 2, Oct. 18, 2016 (Oct. 18, 2016), XP055425797, DOI: 10.15406/jnmr.2016.04.00084, the whole document, see for instance the abstract.
Sharadendu Mishra: "Formulation and evaluation of pH sensitive nanoparticles for colon targeted drug delivery system", Pharmaceutica Analytica Acta, vol. 04, No. 02, Jan. 1, 2013 (Jan. 1, 2013), XP055425839, DOI: 10.4172/2153-2435.S1.018, the whole document, see for instance the abstract.
Konstantinos Lefkimmiatis et al: "cAMP Sponge": A Buffer for Cyclic Adenosine 3', 5'-Monophosphate, PLOS ONE, vol. 4, No. 11, Nov. 3, 2009 (Nov. 3, 2009), page e7649, XP055425564, DOI: 10.1371/journal.pone.0007649, the whole document for instance, the abstract.

*Primary Examiner* — Kristin A Vajda
(74) *Attorney, Agent, or Firm* — Patent Central LLC; Stephan A. Pendorf

(57) ABSTRACT

A means for treating cardiovascular disease, in particular chronic heart failure, especially in terms of a more specific treatment preventing or minimizing pathological hypertrophic signaling while leaving cardiac contractility largely intact. For this purpose the present invention provides a means for treating cardiovascular disease, in particular chronic heart failure, the means specifically inhibiting or causing inhibition of components of the β1-AR/cAMP pathway generating cAMP resulting from activation of the β1-adrenoceptor on the cardiomyocyte cell crest.

14 Claims, 7 Drawing Sheets

MEANS FOR TREATING CARDIOVASCULAR DISEASE

Figure 1:
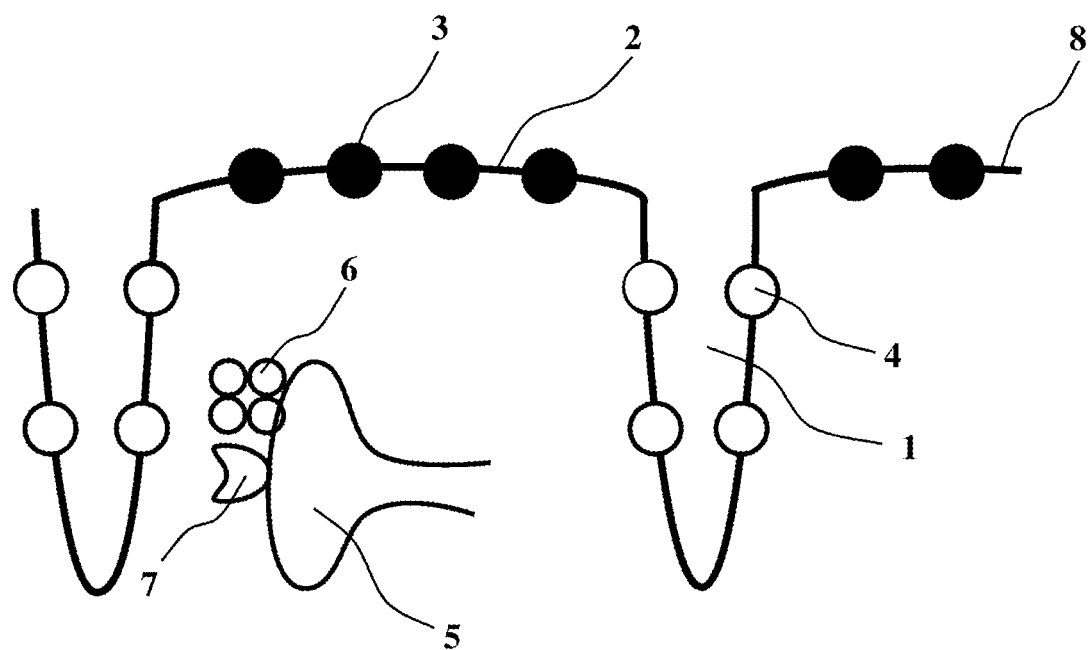

The invention relates to means for treating cardiovascular disease, in particular chronic heart failure (HF), coronary artery disease and cardiac arrhythmias.

Cardiovascular diseases such as chronic heart failure (HF), coronary artery disease and hypertension are among the major causes of death worldwide with a huge global health care burden. Chronic heart failure, for example, affects about 26 million individuals costing yearly approximately 30 billion Euro in the EU alone. Despite modern medication the five year survival of heart failure patients remains at only about 50% (Mosterd, A., Cost, B., Hoes, A. W., de Bruijne, M. C., Deckers, J. W., Hofman, A., & Grobbee, D. E. 2001. The prognosis of heart failure in the general population: The Rotterdam Study. Eur Heart J, 22, 1318-1327; Roger, V. L. 2013. Epidemiology of heart failure. Circ Res, 113, 646-659.). Current therapeutic strategies are primarily aimed at blocking critical neuro-hormonal mechanisms such as hyper-activation of sympathetic nervous and renin-angiotensin-aldosterone systems which crucially contribute to a vicious circle typical for HF pathogenesis (Eschenhagen, T. 2008. Beta-adrenergic signaling in heart failure-adapt or die. Nat Med, 14, 485-487.). With a combination of several therapeutics such as beta blockers (β-blockers), which selectively inhibit cardiac $β_1$-adrenergic receptors ($β_1$-ARs), angiotensin converting enzyme inhibitors or angiotensin receptor blockers, aldosterone receptor antagonists, disease progression can be significantly slowed down (Ponikowski, P., Voors, A. A., Anker, S. D., Bueno, H., Cleland, J. G., Coats, A. J., Falk, V., Gonzalez-Juanatey, J. R., Harjola, V. P., Jankowska, E. A., Jessup, M., Linde, C., Nihoyannopoulos, P., Parissis, J. T., Pieske, B., Riley, J. P., Rosano, G. M., Ruilope, L. M., Ruschitzka, F., Rutten, F. H., van der Meer, P., & Authors/Task Force, M. 2016. 2016 ESC Guidelines for the diagnosis and treatment of acute and chronic heart failure: The Task Force for the diagnosis and treatment of acute and chronic heart failure of the European Society of Cardiology (ESC) Developed with the special contribution of the Heart Failure Association (HFA) of the ESC. Eur Heart J, 37, 2129-2200). In almost all patients, with a few contraindications such as asthma, severe atrioventricular block and acute HF, treatment includes the use of β-blockers. Although recent introduction of additional drugs such as ivabradine (Swedberg, K., Komajda, M., Bohm, M., Borer, J. S., Ford, I., Dubost-Brama, A., Lerebours, G., Tavazzi, L., & Investigators, S. 2010. Ivabradine and outcomes in chronic heart failure (SHIFT): a randomised placebo-controlled study. Lancet, 376, 875-885) and neprilysin inhibitors (McMurray, J. J., Packer, M., Desai, A. S., Gong, J., Lefkowitz, M. P., Rizkala, A. R., Rouleau, J. L., Shi, V. C., Solomon, S. D., Swedberg, K., Zile, M. R., Investigators, P.-H., & Committees. 2014. Angiotensin-neprilysin inhibition versus enalapril in heart failure. N Engl J Med, 371, 993-1004) allowed to decrease mortality by some degree, the classical treatment strategy based on general blockage of neuro-hormonal disease mechanisms seems to have reached an impasse.

$β_1$-AR is coupled to stimulatory G-proteins (Gs) which in turn activate adenylyl cyclases to produce the second messenger cyclic adenosine monophosphate (cAMP). In the heart, cAMP generated in response to catecholamine stimulation of cardiomyocyte (CM) $β_1$-AR modulates excitation-contraction coupling by cAMP-dependent protein kinase (PKA)-mediated phosphorylation of several calcium handling and contractile proteins. For example, phosphorylation of sarcolemmal L-type calcium channels (LTCC) leads to increased $Ca^{2+}$ influx, and of sarcoplasmic ryanodine receptors (RyRs)—to increased systolic $Ca^{2+}$ release from the sarcoplasmic reticulum (SR), collectively responsible for a positive inotropic effect, i.e. an increase in force of contraction. Phosphorylation of phospholamban (PLN), the inhibitor protein for SR Ca-ATPase (SERCA) relieves its inhibition and facilitates diastolic $Ca^{2+}$ reuptake back into SR, improving relaxation (positive lusitropic effect) (Bers, D. M. 2002. Cardiac excitation-contraction coupling. Nature, 415, 198-205). This helps the heart to meet an increased contractility demand upon physical or emotional stress. However, chronic stimulation of the cAMP signaling pathway leads to maladaptive cardiac remodelling (Lohse, M. J., Engelhardt, S., & Eschenhagen, T. 2003. What is the role of beta-adrenergic signaling in heart failure? Circ Res, 93, 896-906). This happens either via protein kinase A (PKA) phosphorylation of several transcription regulators such as CREB and HDAC5 acting in the CM nucleus or via ion channel-dependent $Ca^{2+}$ rise which can stimulate the phosphatase calcineurin and the transcription factor NFAT, triggering hypertrophic gene expression (De Windt, L. J., Lim, H. W., Bueno, O. F., Liang, Q., Delling, U., Braz, J. C., Glascock, B. J., Kimball, T. F., del Monte, F., Hajjar, R. J., & Molkentin, J. D. 2001. Targeted inhibition of calcineurin attenuates cardiac hypertrophy in vivo. Proc Natl Acad Sci USA, 98, 3322-3327; Ha, C. H., Kim, J. Y., Zhao, J., Wang, W., Jhun, B. S., Wong, C., & Jin, Z. G. 2010. PKA phosphorylates histone deacetylase 5 and prevents its nuclear export, leading to the inhibition of gene transcription and cardiomyocyte hypertrophy. Proc Natl Acad Sci USA, 107, 15467-15472; Markou, T., Hadzopoulou-Cladaras, M., & Lazou, A. 2004. Phenylephrine induces activation of CREB in adult rat cardiac myocytes through MSK1 and PKA signaling pathways. J Mol Cell Cardiol, 37, 1001-1011; Weeks, K. L., & Avkiran, M. 2015. Roles and post-translational regulation of cardiac class IIa histone deacetylase isoforms. J Physiol, 593, 1785-1797).

Recently, it has been increasingly recognized that a plethora of diverse and often opposing cAMP mediated effects simultaneously occurring in the cell is possible due to subcellular signalling compartmentation. According to this concept cAMP acts in distinct subcellular microdomains which contain specific pools of localized receptors, PKA on its anchoring proteins, kinase substrates, phosphatases and phosphodiesterases (PDEs), enzymes responsible for local cAMP degradation (Perera, R. K., & Nikolaev, V. O. 2013. Compartmentation of cAMP signalling in cardiomyocytes in health and disease. Acta Physiol (Oxf), 207, 650-662). Each of the above mentioned calcium handling proteins (LTCC, RyR, SERCA) forms its own cAMP microdomain which is differentially regulated and linked to a certain functional outcome (Froese, A., & Nikolaev, V. O. 2015. Imaging alterations of cardiomyocyte cAMP microdomains in disease. Front Pharmacol, 6, 172; Lompre, A. M., Hajjar, R. J., Harding, S. E., Kranias, E. G., Lohse, M. J., & Marks, A. R. 2010. $Ca^{2+}$ cycling and new therapeutic approaches for heart failure. Circulation, 121, 822-830). Likewise, nuclear PKA forms another locale linked to pathological hypertrophy (Haj Slimane, Z., Bedioune, I., Lechene, P., Vain, A., Lefebvre, F., Mateo, P., Domergue-Dupont, V., Dewenter, M., Richter, W., Conti, M., El-Armouche, A., Zhang, J., Fischmeister, R., & Vandecasteele, G. 2014. Control of cytoplasmic and nuclear protein kinase A by phosphodiesterases and phosphatases in cardiac myocytes. Cardiovasc Res, 102, 97-106), while some other microdomains, e.g. controlled by PDE2 have been shown to protect the heart from pathological remodelling (Zoccarato, A., Surdo, N. C., Aronsen, J. M., Fields, L. A., Mancuso, L., Dodoni, G., Stangherlin, A., Livie, C., Jiang, H., Sin, Y. Y., Gesellchen, F., Terrin, A., Baillie, G. S., Nicklin, S. A., Graham, D., Szabo-Fresnais, N., Krall, J., Vandeput, F., Movsesian, M., Furlan, L., Corsetti, V., Hamilton, G., Lefkimmiatis, K., Sjaastad, I., & Zaccolo, M. 2015. Cardiac Hypertrophy Is Inhibited by a Local Pool of cAMP Regulated by Phosphodiesterase 2. Circ Res, 117, 707-719). In addition, two different populations of LTCCs have recently been identified in CMs, one located in caveolar membrane domains and associated with pro-hypertrophic effects, and another one found in non-caveolar membrane domains linked to the regulation of cardiac contractility (Makarewich, C. A., Correll, R. N., Gao, H., Zhang, H., Yang, B., Berretta, R. M., Rizzo, V., Molkentin, J. D., & Houser, S. R. 2012. A caveolae-targeted L-type Ca(2)+ channel antagonist inhibits hypertrophic signaling without reducing cardiac contractility. Circ Res, 110, 669-674).

It is an object of the invention to provide a new therapeutic approach for treating cardiovascular disease, in particular chronic heart failure, especially in terms of a more specific pi-AR/cAMP microdomain based treatment preventing or minimizing pathological hypertrophic signalling while leaving cardiac contractility largely intact.

For this purpose the present invention provides a means for treating cardiovascular disease, in particular chronic heart failure, the means specifically inhibiting or causing inhibiting of components of the $\beta_1$-AR/cAMP pathway generating cAMP resulting from activation of the $\beta_1$-adrenoceptor on the cardiomyocyte cell crest.

It has surprisingly been found that there are at least two distinct populations of cardiomyocyte (CM) $\beta_1$-ARs, one located on the membrane crests and strongly stimulating hypertrophy-associated pools of cAMP, and another one found in T-tubules which is predominantly associated with the regulation of CM contractility. The currently practiced general inhibition of $\beta_1$-AR/cAMP signalling using β-blockers not only leads to reduced pro-hypertrophic signalling (which is the desired effect) but also to less well tolerable decrease in contractility or blockage of other cardioprotective mechanisms. The invention thus provides a new approach for treating cardiovascular disease in a mammal, preferably a human, in particular chronic heart failure, coronary artery disease and cardiac arrhythmias, by specifically targeting disease-promoting $\beta_1$-AR pools in particular subcellular microdomains, or cAMP signalling linked to these disease-promoting $\beta_1$-AR pools. The invention enables more specifically targeted treatment of cardiac dysfunction, for example by selectively blocking distinct functional pools of $\beta_1$-AR associated with negative disease-promoting e.g. hypertrophic effects, while leaving positive $\beta_1$-AR effects on cardiac contractility largely intact. The invention thus provides for means for specifically targeting microdomain-specific $\beta_1$-AR signalling mechanisms, for example specific beta-blockers acting at distinct pathology-associated membrane structures, means for inhibiting receptor-dependent Gs-protein signalling in disease-promoting mirodomains, or means for shutting down local detrimental second messenger (cAMP) signals.

The terms "$\beta_1$-AR" or "beta-$_1$-AR" relate to the beta-1 adrenergic receptor, also referred to as Pi adrenoreceptor, $\beta^1$ adrenoceptor or ADRB1. $\beta_1$-AR is a G-protein coupled receptor (GPCR) associated with the Gs heterotrimeric G-protein, mediating the catecholamine-induced activation of adenylate cyclase. It is membrane-bound and predominantly expressed in cardiac tissue. Natural ligands of $\beta_1$-AR are epinephrine (adrenaline) and norepinephrine (noradrenaline).

The terms "$\beta_1$-AR/cAMP pathway" or "$\beta_1$-AR/cAMP signalling", as used herein, relate to the pathway comprising activation of $\beta_1$-AR by binding of a ligand to the $\beta_1$-AR and the G protein mediated formation of the second messenger cAMP by adenylate cyclase initiated by the activated $\beta_1$-AR. Components of this pathway include the $\beta_1$ adrenergic receptor, Gs proteins coupled to the receptor and adenylate cyclase (adenylyl cyclase, EC 4.6.1.1) class III activated by the Gs protein.

The terms "crest $\beta_1$-AR/cAMP pathway" or "crest $\beta_1$-AR/cAMP signalling" may be used to refer to cAMP generation induced by activation of $\beta_1$-AR located on the cell crest, and the terms "T-tubule $\beta_1$-AR/cAMP pathway" or "T-tubule $\beta_1$-AR/cAMP signalling" be used to refer to cAMP generation induced by activation of $\beta_1$-AR in T-tubules.

The term "means specifically inhibiting or causing inhibition of components of the $\beta_1$-AR/cAMP pathway generating cAMP resulting from activation of the $\beta_1$-adrenoceptor on the cardiomyocyte cell crest" relates to compounds, compositions of compounds or genetic constructs at least predominantly, if not exclusively, inhibiting or causing inhibition of at least one of the components of the $\beta_1$-AR/cAMP pathway leading to cAMP formation resulting from activation of the $\beta_1$-adrenoceptor on the cardiomyocyte cell crest (crest $\beta_1$-AR/cAMP pathway). A beta-blocker blocking the respective $\beta_1$-AR, i.e. preventing activation of the $\beta_1$-AR by ligand binding, is an example of such a means. The term also encompasses carriers, e.g. nanoparticles, carrying, covalently linked to or coated with such a means, for example a beta-blocker. In particular, "specifically inhibiting" here means that, in the presence of a means of the invention, the amount of cAMP generated by the crest $\beta_1$-AR/cAMP pathway is at least 50%, preferably 60%, 70%, 80%, 85%, 90% or especially preferred at least 95% reduced compared to the uninhibited pathway, and that the amount of cAMP generated by the T-tubule $\beta_1$-AR/cAMP pathway is, at the same time, preferably essentially unchanged or remains at a level of no less than 60%, 70%, 80%, 90% or 95% below the level in the absence of the means. The term "coated with" in relation to a means of the invention means that a surface of a carrier has at least one layer of a compound or composition comprising a means of the invention in immobilized form, such that the means, e.g. a blocker, is not or at least essentially not released from the coating.

The term "β blocker" or "beta blocker" relates to compounds binding to and blocking a beta adrenergic receptor, e.g. the beta-1 adrenergic receptor. The term thus refers to antagonists or inverse agonists of beta adrenergic receptors. Examples of known beta blockers selective for $\beta_1$-AR are acebutolol, atenolol, betaxolol, bisoprolol, esmolol, metoprolol and nebivolol. Examples of unspecific beta blockers blocking $\beta_1$- and $\beta_2$-AR are propranolol, pindolol and carvedilol.

The term "cardiovascular disease" (CVD) relates to a class of disorders of the heart and blood vessels, including, for example, coronary artery disease, cardiac arrhythmias, and heart failure (HF), also referred to as "chronic heart failure" or "congestive heart failure" (CHF).

The term "T-tubules" relates to invaginations of the sarcolemma (muscle cell membrane) penetrating into the centre of skeletal and cardiac muscle cells.

The terms "cardiomyocyte cell crest", "cell crest" or "crest" relate to exterior regions of the cardiomyocyte sarcolemma, i.e. regions of the heart muscle cell membrane which are not part of invaginations, in particular not part of T-tubules.

The term "FRET" (abbreviation for "Förster resonance energy transfer" or "fluorescence resonance energy transfer") relates to an energy transfer between two chromophores, a donor chromophore transferring energy to an acceptor chromophore through nonradiative dipole-dipole coupling.

The term "scanning ion conductance microscopy" (SICM) relates to a non-optical imaging technique which uses a glass nanopipette (e.g. ~30-50 nm diameter, ~100 MΩ resistance) as a scanning probe for non-contact precise visualization of membrane topography of a living cell and for applying pharmacological ligands onto clearly defined membrane structures such as single T-tubules and cell crests.

In a first aspect the invention provides a means for treating cardiovascular disease, in particular chronic heart failure, the means specifically inhibiting or causing inhibition of components of the $β_1$-AR/cAMP pathway generating cAMP resulting from activation of the $β_1$-adrenoceptor on the cardiomyocyte cell crest.

In a preferred embodiment the means of the invention is a beta blocker specifically blocking the $β_1$-adrenoceptor on the cardiomyocyte cell crest.

In a further preferred embodiment the means of the invention is a binding molecule specifically binding to and blocking the $β_1$-adrenoceptor on the cardiomyocyte cell crest. The binding molecule can, for example, be an antibody, preferably a monoclonal antibody, or an aptamer specifically binding to and blocking the $β_1$-adrenoceptor on the cardiomyocyte cell crest. Aptamers are short synthetic single-stranded DNA or RNA oligonucleotides capable of highly-specific antibody-like binding to target molecules, for example, proteins like the $β_1$-adrenoceptor. Compared to antibodies, aptamers have low immunogenicity with high specificity and affinity as well as chemical stability. Aptamers can be selected, for example, by means of a method called SELEX (systematic evolution of ligands by exponential enrichment) (Ellington and Szostak (1990), Nature 346, 818-822; Gopinath (2007), Anal Bioanal Chem 387, 171-182, WO 91/19813).

The means of the invention may also be a binding molecule complex, e.g. an antibody complex, i.e. a complex comprising multiple entities of the same or different binding molecules, for example antibodies. Preferably, the complex is large enough to not being able to enter T-tubules. Such a complex could, for example, comprise 5 to 10 antibodies, and would act at the crest but would not enter T-tubules.

In a further preferred embodiment, the means of the invention is a carrier, e.g. a nanoparticle, having a suitable size to be excluded from entry into T-tubules, e.g. a gold or plastic nanoparticle having a diameter of more than 11 nm, and being coated with or carrying a covalently bound a beta-blocker or a binding molecule specifically blocking the $β_1$-adrenoceptor, preferably specifically blocking the $β_1$-adrenoceptor on the cardiomyocyte cell crest. Functionalized carriers like nanoparticles, e.g. plastic or gold nanoparticles, are especially suitable in the context of the invention, because they can be designed or chosen, in particular in view of their diameter, to not be able to enter T-tubules due to size restrictions. Thus it is possible to specifically block receptors located at the outer membrane in the crest, because nanoparticles of suitable size will not be able to enter the T-tubules via their approximately 200 nm large openings. Suitable nanoparticles are, for example, gold or plastic nanoparticles with a shell coated with a β-blocker. For the functionalization of nanoparticles an unselective β-blocker like propranolol could also be used. It has been shown that gold nanoparticles of the size >11 nm are not able to enter the CM T-tubular system (Parfenov, A. S., Salnikov, V., Lederer, W. J., & Lukyanenko, V. 2006, Aqueous diffusion pathways as a part of the ventricular cell ultrastructure. Biophys J, 90, 1107-1119), so that they should act exclusively on crest-located receptors. Gold nanoparticles or uncharged synthetic nanoparticles are advantageous, because they have a much higher inertness and lower rates of endocytosis compared to, for example, synthetic positively or negatively charged carboxyl-modified polystyrene latex nanoparticles. Positively charged carboxyl-modified polystyrene latex nanoparticles have been shown to be cytotoxic and disrupt the integrity of CM membrane, while the negatively charged nanoparticles can induce nanopore formation and arrythmias due to their charge (Miragoli, M., Novak, P., Ruenraroengsak, P., Shevchuk, A. I., Korchev, Y. E., Lab, M. J., Tetley, T. D., & Gorelik, J. 2013. Functional interaction between charged nanoparticles and cardiac tissue: a new paradigm for cardiac arrhythmia? Nanomedicine (Lond), 8, 725-737). Other types of functionalized nanoparticles, such as (for example approximately 200 nm) carboxyl-modified particles (Novak, P., Shevchuk, A., Ruenraroengsak, P., Miragoli, M., Thorley, A. J., Klenerman, D., Lab, M. J., Tetley, T. D., Gorelik, J., & Korchev, Y. E. 2014, Imaging single nanoparticle interactions with human lung cells using fast ion conductance microscopy. Nano Lett, 14, 1202-1207) which do not damage CM membranes and are covalently linked to or are coated with, for example, $β_1$-AR selective blockers can also be used. The nanoparticles may also be functionalized with binding molecules like antibodies or aptamers.

Alternatively, a genetically encoded inhibitor of the $β_1$-AR/cAMP pathway engineered to localize at the cell crest such as a dominant-negative Gs-protein (Berlot, C. H. 2002, A highly effective dominant negative alpha s construct containing mutations that affect distinct functions inhibits multiple Gs-coupled receptor signaling pathways. J Biol Chem, 277, 21080-21085) or a cAMP "sponge" (Lefkimmiatis, K., Moyer, M. P., Curci, S., & Hofer, A. M. (2009). "cAMP sponge": a buffer for cyclic adenosine 3', 5'-monophosphate. PLoS One, 4, e7649.) can also be used. These means can specifically inhibit cAMP generation by the $β_1$-AR localized on the cell crest or buffer larger amounts of cAMP produced by this pathway.

Further, the means of the invention can be a pH-dependent beta-blocker acting specifically or at least preferably on crest $β_1$-AR due to a difference in pH in the cell crest compared to T-tubules. Due to differential expression of pH regulating ion transporters in T-tubules vs. later membrane (cell crest) both locations have been shown to generate different pH grandients (Garciarena C D, Ma Y, Swietach P, Huc L, Vaughan-Jones R D. Sarcolemmal localisation of $Na^+/H^+$ exchange and $Na^+$—$HCO_3^-$ co-transport influences the spatial regulation of intracellular pH in rat ventricular myocytes. The Journal of Physiology. 2013; 591 (Pt 9):2287-2306. doi:10.1113/jphysiol.2012.249664). A beta-blocker designed to have a lower or no activity at the pH in T-tubules is thus also envisioned as a means of the invention. The term "pH-dependent beta blocker" relates to a beta blocker the blocking activity of which depends on pH.

In second aspect, the invention relates to a medicamtent comprising at least one of the means of the first aspect of the invention. The medicament preferably further comprises suitable excipients and adjuvants. Such excipients and adjuvants are known to the skilled person.

In still another aspect the invention relates to a method for therapeutic treatment of a cardiovascular disease, especially chronic heart failure, comprising administering to a patient in need of such treatment a therapeutically effective amount of a means according to the first aspect of the invention or of a medicament according to the second aspect of the invention.

In the following, the invention is described for illustration purposes only in more detail.

FIG. 1 Simplified and schematic cross-sectional view of a part of a cardiomyocyte (CM) showing T-tubules and crest regions of the sarcolemma with crest $\beta_1$-ARs (large closed circles) and T-tubular $\beta_1$-ARs (large open circles) and part of the SR (sarcoplasmic reticulum) with Protein kinase A type II (PKA II) and phosphodiesterase type 4 (PDE4).

Figure 2:
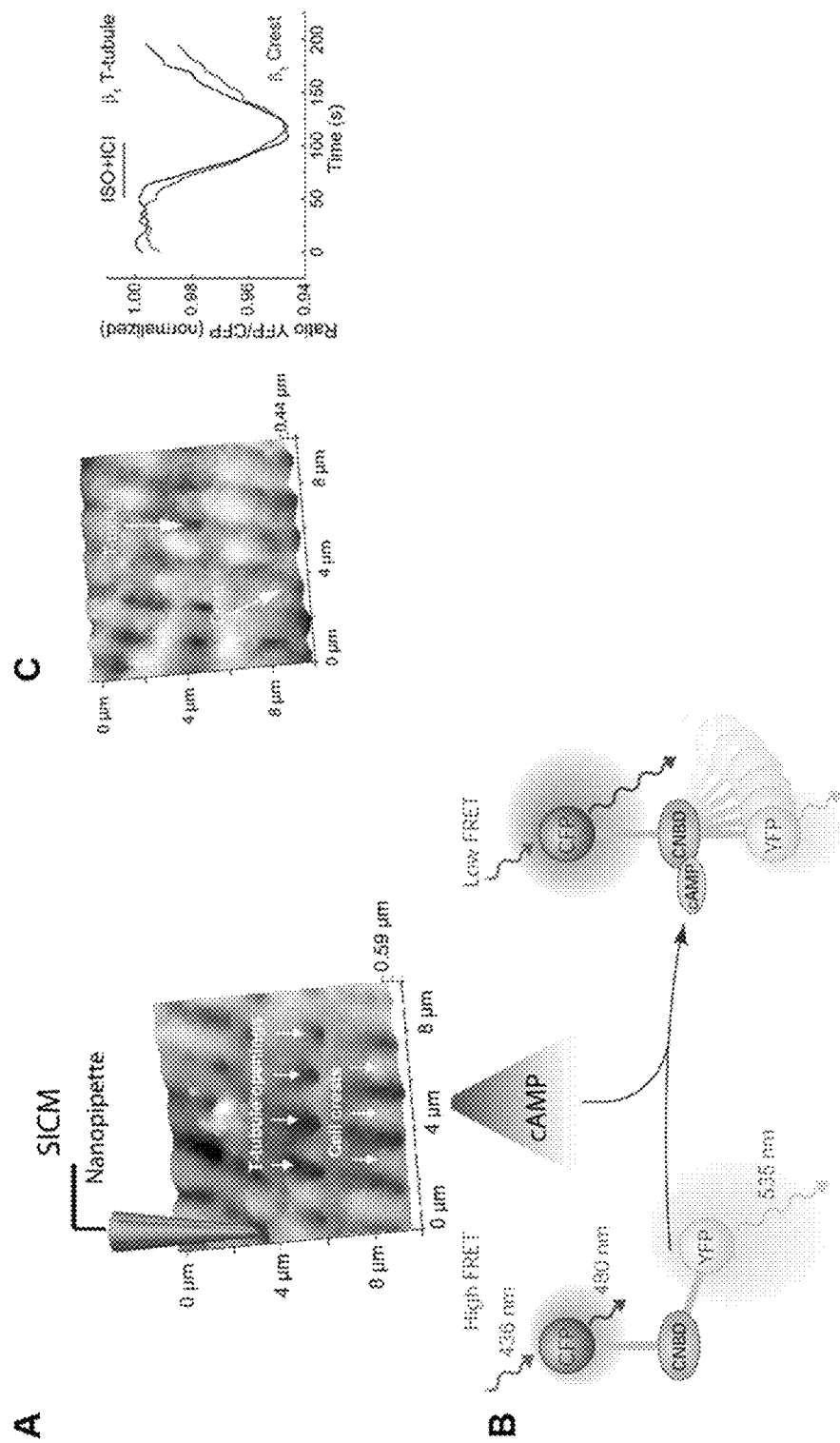

FIG. 2 Principle of the scanning ion conductance microscopy (SICM) combined with a FRET biosensor for cAMP (A). This technique uses a ligand containing nanopipette (size ~50 nm) for localization and precise local stimulation of $\beta$-AR populations at different CM membrane structures such as T-tubuli and cell crests. B. Receptor-triggered cAMP signals are detected intracellularly by a cytosolic FRET based biosensor. C. This technique showed that $\beta_1$-AR is located in both T-tubuli and crests and that both receptor pools activate cytosolic cAMP synthesis to a similar degree. ISO, $\beta$-AR agonist isoproterenol. ICI, $\beta_2$-AR blocker ICI 118,551 locally applied via SICM pipette to marked locations (white arrows).

Figure 3:
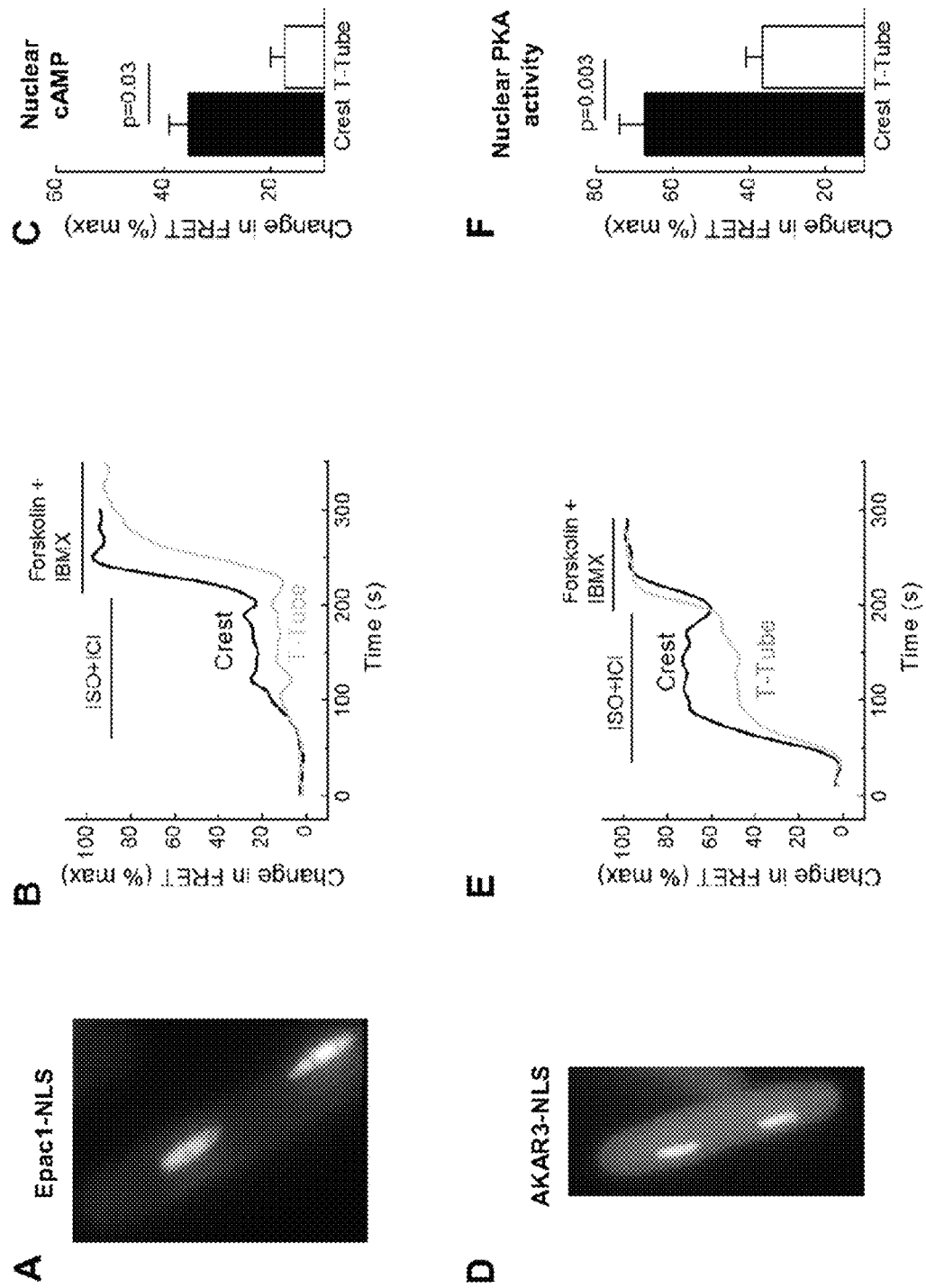

FIG. 3 Two distinct $\beta_1$-AR populations revealed by SICM/FRET. A-C. Rat ventricular CMs expressing nuclear localized Epac1-NLS sensor show stronger $\beta_1$-AR/cAMP responses stimulated by the crest than T-tubular pool of receptors. D-F. The same cells expressing a nuclear PKA activity reporter AKAR3-NLS show much stronger nuclear PKA activity induced by $\beta_1$-AR located in the crest, as compared to receptors stimulated in the T-tubules.

Figure 4:
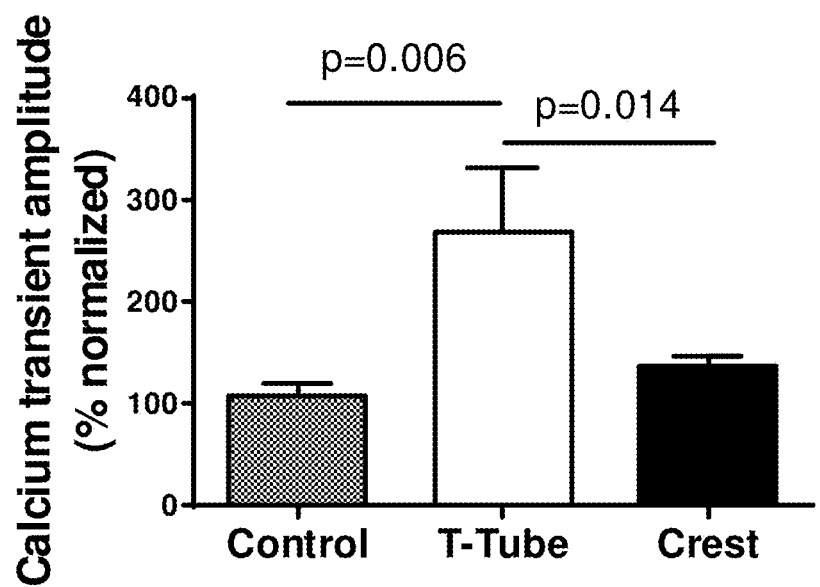

FIG. 4 Cardiomyocyte contractility responses measured as an amplitude of calcium transient upon application of $\beta_1$-AR stimulus (ISO+ICI) to T-tubuli or cell crests. Calcium transients are much stronger stimulated by T-tubular $\beta_1$-AR suggesting that this receptor pool is more strongly involved in the regulation of cellular contractility.

Figure 5:
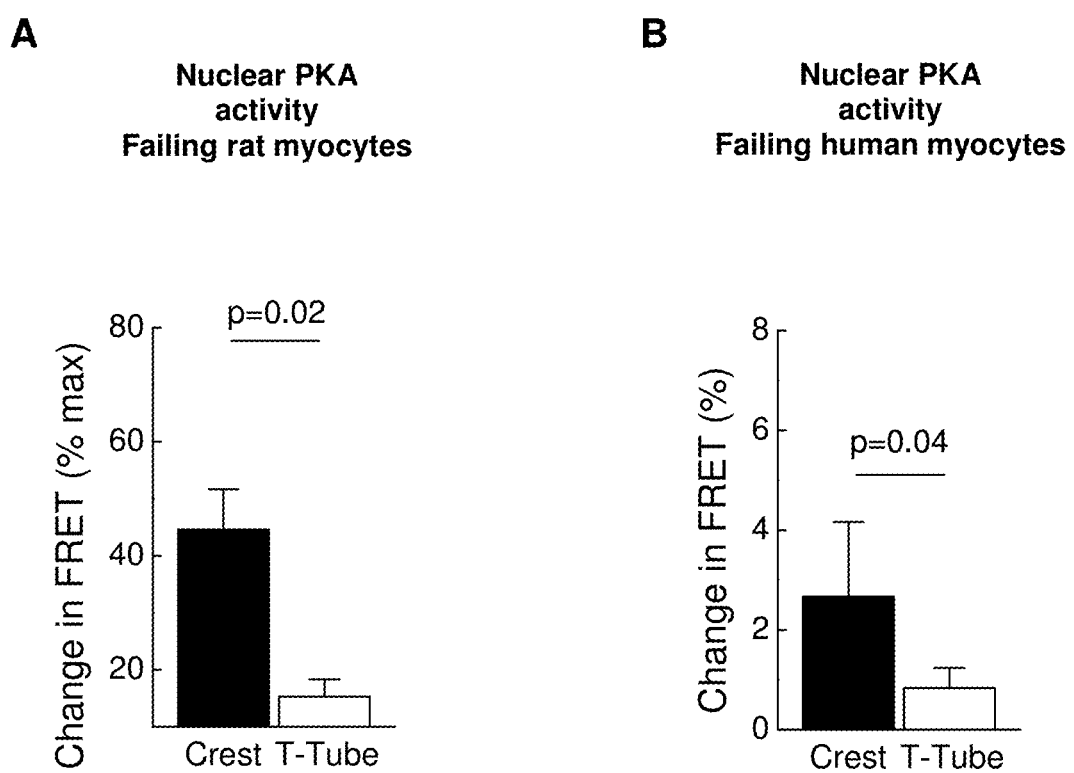

FIG. 5. Measurements of nuclear PKA activity in failing ventricular cardiomyocytes isolated from rats with a chronic heart failure model 16 weeks after myocardial infarction (A) and from patients with hypertrophic cardiomyopathy undergoing aortic valve replacement surgery. SICM/FRET measurements were performed as described in FIG. 3D-F.

Figure 6:
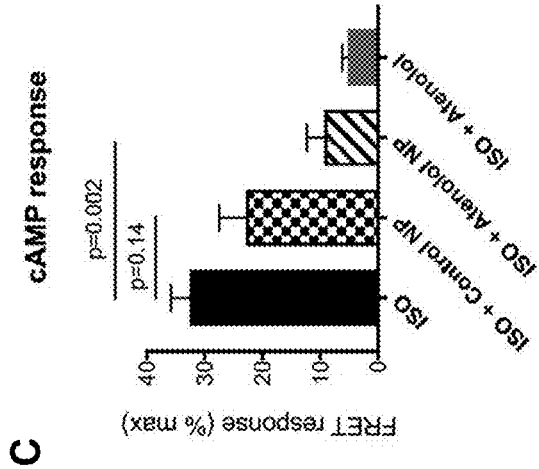
Figure 6:
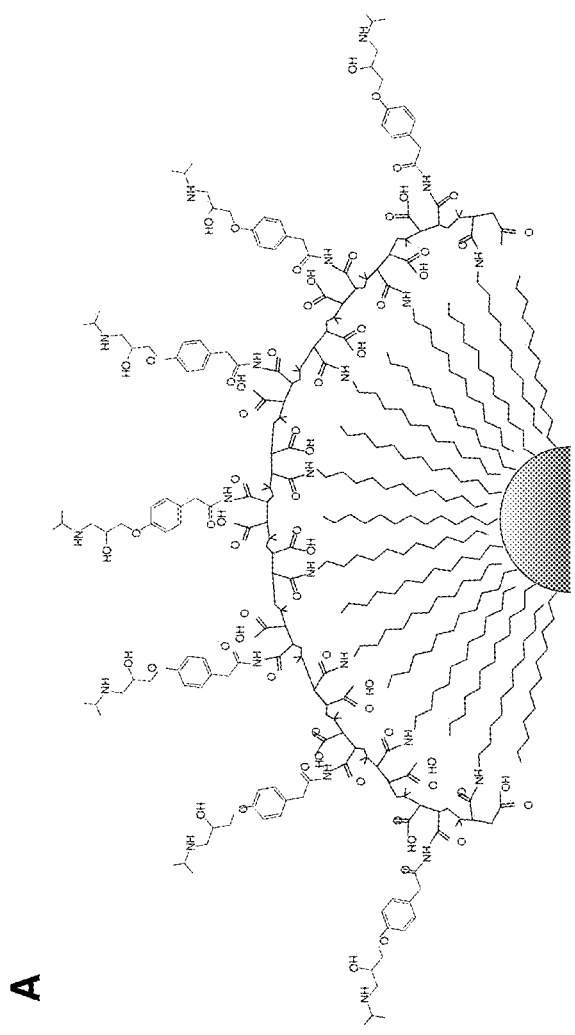
Figure 6:
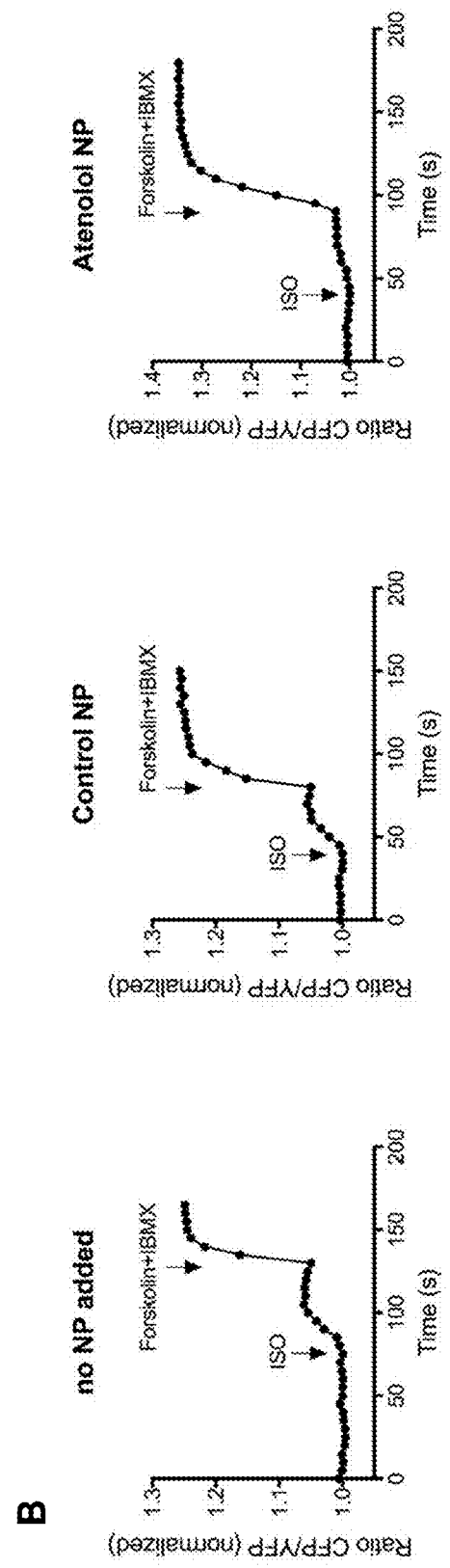

FIG. 6. Pharmacological characterization of atenolol coated nanoparticles (NP). A. Schematic representation of an atenolol coated gold nanoparticle. B-C. Experimental data with HEK293 cells stably expressing $\beta_1$-AR and the cAMP biosensor Epac1-camps. Using FRET-based cAMP assay it could be shown that atenolol coated (Atenolol NP) but not bare control (Contol NP) effectively inhibit ISO-induced cAMP increase.

Figure 7:
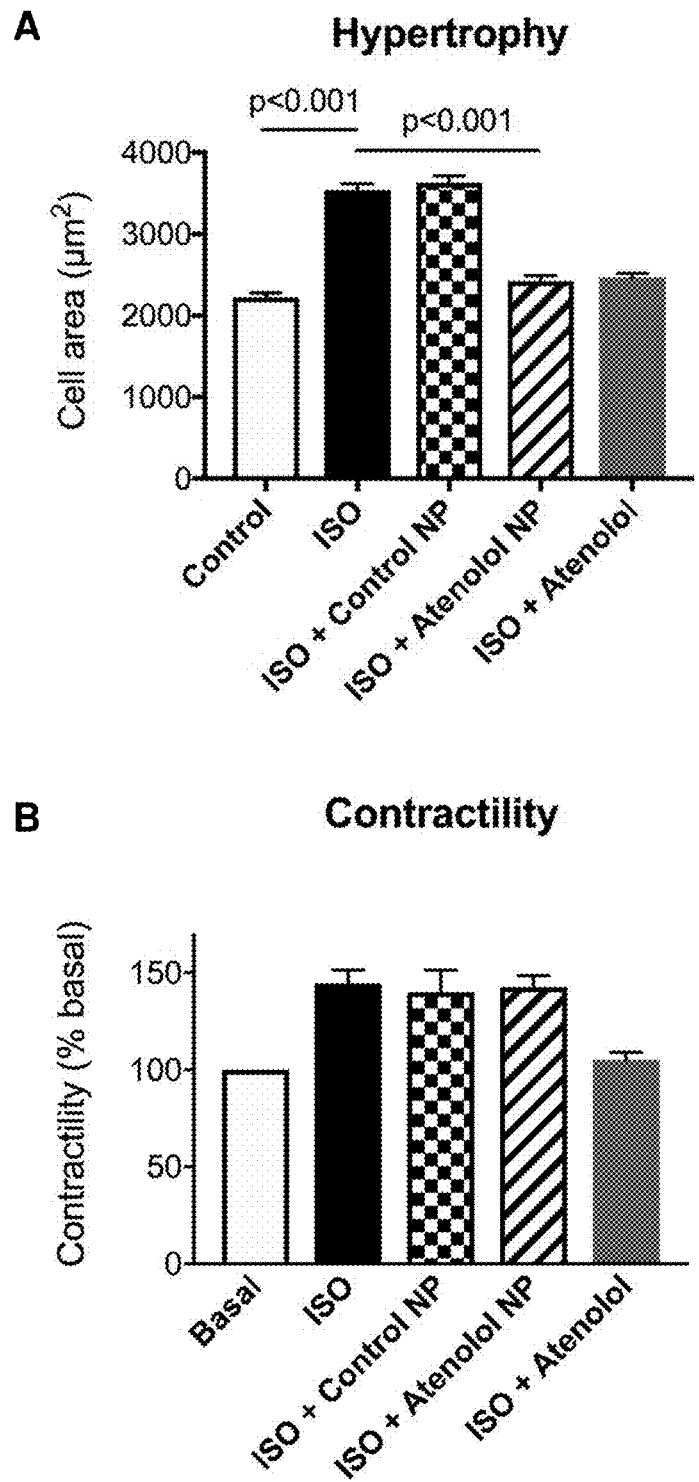

FIG. 7. Experimental data for cardiomyocyte hypertrophy (A) and cell contractility (B) assays performed with freshly isolated adult rat ventricular cardiomyocytes (CM) using atenolol coated nanoparticles (Atenolol NP) and control nanoparticles. Atenolol NP can block cardiomyocyte hypertrophy but do not inhibit contractility.

FIG. 1 shows a simplified and schematic cross-sectional view of a part of a cardiomyocyte (CM). FIG. 1 shows T-tubules 1 being invaginations of the sarcolemma 8 and crest regions 2 of the sarcolemma 8 with $\beta_1$-ARs 3 (large closed circles) and T-tubular $\beta_1$-ARs 4 (large open circles) and part of the SR 5 (sarcoplasmic reticulum) with Protein kinase A type II 6 (PKA II) and phosphodiesterase type 4 7 (PDE4).

To study functional $\beta$-AR localization, a combination of scanning ion conductance microscopy (SICM) with FRET based recording of intracellular cAMP called SICM/FRET was used (Nikolaev, V. O., Moshkov, A., Lyon, A. R., Miragoli, M., Novak, P., Paur, H., Lohse, M. J., Korchev, Y. E., Harding, S. E., & Gorelik, J. 2010. Beta2-adrenergic receptor redistribution in heart failure changes cAMP compartmentation. Science, 327, 1653-1657) (FIG. 2). This method allows imaging of live CM membrane structures and associated signalling with nanometre precision. Real time dynamics of cAMP in intact cardiomyocytes (CMs) can be studied using highly sensitive biosensors based on Förster Resonance Energy Transfer (FRET). Such sensors contain a single cyclic nucleotide binding domain fused to a pair of fluorescent proteins and change their conformation upon cAMP binding (Nikolaev, V. O., Bunemann, M., Hein, L., Hannawacker, A., & Lohse, M. J. 2004. Novel single chain cAMP sensors for receptor-induced signal propagation. J Biol Chem, 279, 37215-37218), resulting in a decrease of FRET (FIG. 2B). They can be expressed in transgenic animals in CM-specific (Nikolaev, V. O., Bünemann, M., Schmitteckert, E., Lohse, M. J., & Engelhardt, S. 2006. Cyclic AMP imaging in adult cardiac myocytes reveals far-reaching beta1-adrenergic but locally confined beta2-adrenergic receptor-mediated signaling. Circ Res, 99, 1084-1091) and ubiquitous manner (Calebiro, D., Nikolaev, V. O., Gagliani, M. C., de Filippis, T., Dees, C., Tacchetti, C., Persani, L., & Lohse, M. J. 2009. Persistent cAMP-signals triggered by internalized G-protein-coupled receptors. PLoS Biol, 7, e1000172.) to allow live cell cAMP imaging with unprecedented spatio-temporal resolution. Interestingly, when using such cytosolic cAMP biosensor in SICM/FRET experiments upon local activation of $\beta_1$-ARs in T-tubules or on cell crests, no difference in cytosolic $\beta_1$AR/cAMP responses between these two receptor pools could be observed (FIG. 2C). Recently, several localized versions of cAMP biosensors targeted to the proximity of major Ca-handling proteins such as LTCC, RyR and SERCA (Perera, R. K., Sprenger, J. U., Steinbrecher, J. H., Hubscher, D., Lehnart, S. E., Abesser, M., Schuh, K., El-Armouche, A., & Nikolaev, V. O. 2015. Microdomain switch of cGMP-regulated phosphodiesterases leads to ANP-induced augmentation of beta-adrenoceptor-stimulated contractility in early cardiac hypertrophy. Circ Res, 116, 1304-1311; Sprenger, J. U., Perera, R. K., Steinbrecher, J. H., Lehnart, S. E., Maier, L. S., Hasenfuss, G., & Nikolaev, V. O. 2015. In vivo model with targeted cAMP biosensor reveals changes in receptor-microdomain communication in cardiac disease. Nat Commun, 6, 6965) and to the nucleus have been developed. This allowed microdomain-specific imaging of real time cAMP dynamics. Using these microscopy tools combined with an in vivo mouse model of early HF, it could be uncovered that the disease leads to redistribution of several PDEs between different membrane domains associated with T-tubuli which affects $\beta_1$-AR stimulated cardiac contractility (Perera, R. K., Sprenger, J. U., Steinbrecher, J. H., Hubscher, D., Lehnart, S. E., Abesser, M., Schuh, K., El-Armouche, A., & Nikolaev, V. O. 2015. Microdomain switch of cGMP-regulated phosphodiesterases leads to ANP-induced augmentation of beta-adrenoceptor-stimulated contractility in early cardiac hypertrophy. Circ Res, 116, 1304-1311). Early HF also leads to an impairment of the direct $\beta_1$-AR—SERCA microdomain communication (Sprenger, J. U., Perera, R. K., Steinbrecher, J. H., Lehnart, S. E., Maier, L. S., Hasenfuss, G., & Nikolaev, V. O. 2015. In vivo model with targeted cAMP biosensor reveals changes in receptor-microdomain communication in cardiac disease. Nat Commun, 6, 6965), further contributing to the contractile dysfunction.

To test the hypothesis, that there are at least two distinct populations of $\beta_1$-ARs, one located on the crest and stronger stimulating hypertrophy-associated pools of cAMP, and another one found in T-tubules which is predominantly associated with the regulation of CM contractility, a nuclear targeted cAMP sensor Epac1-NLS and a nuclear targeted PKA activity reporter AKAR3-NLS (Haj Slimane, Z., Bedioune, I., Lechene, P., Vain, A., Lefebvre, F., Mateo, P., Domergue-Dupont, V., Dewenter, M., Richter, W., Conti, M., El-Armouche, A., Zhang, J., Fischmeister, R., & Vandecasteele, G. 2014. Control of cytoplasmic and nuclear protein kinase A by phosphodiesterases and phosphatases in cardiac myocytes. Cardiovasc Res, 102, 97-106) were used in SICM/FRET experiments under local $\beta_1$-AR stimulation in either cardiomyocyte crests or T-tubules. Using these sensors, it could clearly be shown that $\beta_1$-ARs stimulated at the crest increased cAMP (FIGS. 3A-C) and PKA activity (FIG. 3D-F) in the nucleus much stronger than the receptors stimulated in T-tubules, suggesting that $\beta_1$-AR pool located on the crest is directly associated with the pathological cAMP signalling. In contrast, stimulation of $\beta_1$-ARs localized in T-tubules led to much stronger contractile responses than those measured after receptor stimulation on cell crests (FIG. 4).

In order to be applicable in terms of possible medication, the above mentioned mechanism involving two $\beta_1$-AR receptor pools should be active not only in healthy but also in failing myocytes. FIG. 5 shows SICM/FRET experiments performed as described in FIG. 3D-F with failing rat (FIG. 5A) and failing human (FIG. 5B) myocytes. In both cases, a similar clear difference between receptors stimulated on the crests and in T-tubuli can still be observed. This suggests that the disease, apart from some desensitization (reduction of signal amplitude) does not change the therapeutically interesting pi-AR/cAMP pools targeted by the means of this invention.

FIGS. 6 and 7 show experimental data with beta-blocker coated nanoparticles.

For the preparation of beta-blocker coated nanoparticles 18 nm gold nanoparticles were coated using an amphiphilic polymer poly(isobutylene-alt-maleic anhydride) which was covalently linked to atenolol. Alkylamine chains of the polymer backbone were chemically linked by the direct amidation between maleic anhydride and the amino-ligand dodecylamine which exhibits hydrophobic interaction with gold nanoparticle (Lin, C. A., Sperling, R. A.; Li, J. K.; Yang, T. Y.; Li, P. Y.; Zanella, M.; Chang, W. H.; Parak, W. J., Design of an amphiphilic polymer for nanoparticle coating and functionalization. Small 2008, 4, 334-341). In the second reaction step, atenolol was covalently bound to the polymer via aminogroup and direct amidation (FIG. 6A). The chemicals were typically used at the ratio 2:1:0.5 or 2:1:2 of maleic anhydride/dodecylamine/atenolol. After the synthesis, coated particles were washed, characterized for their size and stability, while last washthrough steps were tested for the absence of atenolol.

FIG. 6B shows the pharmacological characterization of nanoparticles in HEK293 cells stably expressing $\beta_1$-ARs using a FRET-based cAMP assay. Addition of the beta-adrenergic agonist isoproterenol (ISO, 0.1 nM) leads to an increase of CFP/YFP ratio indicating an increase in intracellular cAMP. This increase is blocked by pretreatment (20 min) with 30 nM of atenolol coated nanoparticles, while uncoated control 18 nm gold nanoparticles have no effect. Data analysis for these experiments is presented in FIG. 6C. Atenolol coated nanoparticles are almost as efficacious in blocking $\beta_1$-AR dependent cAMP synthesis as the pure beta-blocker atenolol (used at 30 nM).

Further experiments with adult rat ventricular CMs were performed in order to evaluate the effect of beta-blocker coated nanoparticles on hypertrophy and cell contractility (see FIG. 7). Freshly isolated adult rat ventricular CMs were cultured for one day and preincubated for 1 hour with bare gold 18 nm nanoparticles (Control NP) or 18 nm gold nanoparticles coated with covalently bound beta-blocker atenolol (Atenolol NP) both at 30 nM. To induce hypertrophy, CMs were then concomitantly stimulated for 24 h with 10 nM isoproterenol (ISO). Cell surface areas were then measured for 80 cells per group. The experiments showed that atenolol coated nanoparticles prevent cardiomyocyte hypertrophy (FIG. 7A).

Freshly isolated adult rat ventricular CMs were incubated for 20 min with atenolol (100 nM), atenolol coated or control nanoparticles (both at 30 nM) and cell contractility was measured using edge detection method (IonOptix) at 1 Hz pacing frequency with and without stimulation with 10 nM isoproterenol. The experiments showed that atenolol coated nanoparticles in contrast to pure atenolol do not decrease cell contractility (FIG. 7B).

The invention claimed is:

1. A $\beta$1-AR/cAMP microdomain based therapeutic for preventing or minimizing pathological hypertrophic signalling while leaving cardiac contractility largely intact, comprising
   a) a carrier carrying immobilized on its surface a binding molecule specifically blocking the $\beta$1-adrenoceptor, the binding molecule being selected from beta-blockers, antibodies and aptamers, the carrier having a size excluding it from entering T-tubules, or
   b) a complex of a binding molecule, the binding molecule being selected from antibodies specifically blocking the $\beta$1-adrenoceptor, the complex having a size excluding it from entering T-tubules.

2. The therapeutic according to claim 1, wherein the binding molecule is a beta blocker specifically blocking the $\beta_1$-adrenoceptor on the cardiomyocyte cell crest.

3. The therapeutic according to claim 1, wherein the binding molecule is a binding molecule specifically binding to and blocking the $\beta_1$-adrenoceptor on the cardiomyocyte cell crest.

4. The therapeutic according to claim 3, wherein the binding molecule is an antibody or an aptamer specifically binding to and blocking the $\beta_1$-adrenoceptor on the cardiomyocyte cell crest.

5. The therapeutic s according to claim 1, wherein the therapeutic is a nanoparticle having a diameter of more than 11 nm and carrying immobilized on its surface a binding molecule specifically blocking the $\beta_1$-adrenoceptor.

6. The therapeutic according to claim 1, the binding molecule being a genetically encoded inhibitor of the $\beta_1$-AR/cAMP pathway engineered to localize at the cell crest.

7. The therapeutic according to claim 1, the binding molecule being a pH dependent beta-blocker specifically inhibiting the $\beta_1$-adrenoceptor on the cardiomyocyte cell crest.

8. A medicament comprising a therapeutic according to claim 1.

9. A $\beta$1-AR/cAMP microdomain based method of therapeutic treatment for preventing or minimizing pathological hypertrophic signalling while leaving cardiac contractility largely intact, comprising administering to a patient in need of such treatment a therapeutically effective amount of
- a) a carrier carrying immobilized on its surface a binding molecule specifically blocking the β1-adrenoceptor, the binding molecule being selected from beta-blockers, antibodies and aptamers, the carrier having a size excluding it from entering T-tubules, or
- b) a complex of a binding molecule, the binding molecule being selected from antibodies specifically blocking the β1-adrenoceptor, the complex having a size excluding it from entering T-tubules.

10. The method of therapeutic treatment according to claim 9, wherein the cardiovascular disease is chronic heart failure.

11. The method of therapeutic treatment according to claim 9, wherein the cardiovascular disease is coronary artery disease or cardiac arrhythmias.

12. The therapeutic according to claim 4, wherein the antibody is a monoclonal antibody.

13. The therapeutic according to claim 1, the therapeutic being or comprising a carrier carrying covalently bound on its surface a binding molecule specifically blocking the $\beta_1$-adrenoceptor, the carrier having a size excluding it from entering T-tubules.

14. The therapeutic according to claim 1, wherein the therapeutic is a nanoparticle having a diameter of more than 11 nm and carrying covalently bound on its surface a binding molecule specifically blocking the $\beta_1$-adrenoceptor.

\* \* \* \* \*